(12) United States Patent
Souza (10) Patent No.: US 10,407,660 B2
(45) Date of Patent: *Sep. 10, 2019

(54) HARDWARE FOR MAGNETIC 3D CULTURE

(71) Applicant: GREINER BIO-ONE NORTH AMERICA, INC., Monroe, NC (US)

(72) Inventor: Glauco Souza, Houston, TX (US)

(73) Assignee: Greiner Bio-One North America, Inc., Monroe, NC (US)

(*) Notice: Subject to any disclaimer, the term of this patent is extended or adjusted under 35 U.S.C. 154(b) by 175 days.

This patent is subject to a terminal disclaimer.

(21) Appl. No.: 13/762,103

(22) Filed: Feb. 7, 2013

(65) Prior Publication Data

US 2014/0220672 A1 Aug. 7, 2014
US 2015/0275165 A9 Oct. 1, 2015

Related U.S. Application Data

(63) Continuation of application No. PCT/US2011/046183, filed on Aug. 2, 2011.

(Continued)

(51) Int. Cl.
*C12M 1/00* (2006.01)
*C12M 1/32* (2006.01)
(Continued)

(52) U.S. Cl.
CPC .............. *C12M 47/02* (2013.01); *B01L 3/021* (2013.01); *B01L 3/0289* (2013.01); *C12M 23/10* (2013.01);
(Continued)

(58) Field of Classification Search
CPC ...... B01L 3/021; B01L 3/0217; B01L 3/0289; B01L 2200/0657; B01L 2300/0838; B01L 2400/043; C12M 47/02; C12M 23/10; C12M 23/12; C12M 23/38; C12M 33/04; C12M 35/06
(Continued)

(56) References Cited

U.S. PATENT DOCUMENTS 3,165,450 A * 1/1965 Scheidt .................. C12M 23/10
435/305.3
4,438,068 A * 3/1984 Forrest ...................... B01L 9/06
422/430
(Continued)

FOREIGN PATENT DOCUMENTS

GB 904041 A * 8/1962 ............. A61F 17/00
JP 2004254519 A * 9/2004 ........... C12N 5/0697
(Continued)

OTHER PUBLICATIONS

Wang, Tissue growth in 3D without protein matrixes, Dec. 2011. http://nextbigfuture.com/2011/12/tissue-growth-in-3d-without-protein.html.*

(Continued)

*Primary Examiner* — Liban M Hassan
(74) *Attorney, Agent, or Firm* — Boulware & Valoir (57) ABSTRACT

Devices for magnetic 3d culture are described including magnetic lids/bases for single Petri plates, adjustable height cap for same, as well similar devices for multi-magnet culture plates. A pen-like device for sterilely lifting and moving cells is also described, and this magnetic pipettor can also exist in multi-well magnetic pipettor formats.

12 Claims, 10 Drawing Sheets

Related U.S. Application Data (60) Provisional application No. 61/372,164, filed on Aug. 10, 2010.

(51) Int. Cl.

| | | |
|---|---|---|
| *C12N 13/00* | (2006.01) | |
| *B01L 3/02* | (2006.01) | |
| *C12M 1/22* | (2006.01) | |
| *C12M 1/26* | (2006.01) | |
| *C12M 1/42* | (2006.01) | |
| *C12M 1/12* | (2006.01) | |
| *C12N 5/00* | (2006.01) | |

(52) U.S. Cl.
CPC .......... *C12M 23/12* (2013.01); *C12M 23/38* (2013.01); *C12M 33/04* (2013.01); *C12M 35/06* (2013.01); *B01L 3/0217* (2013.01); *B01L 2200/0657* (2013.01); *B01L 2300/0838* (2013.01); *B01L 2400/043* (2013.01)

(58) Field of Classification Search
USPC ......... 435/305.3, 289.1, 308.1, 173.1, 283.1, 435/305.4; 29/428, 453
See application file for complete search history.

(56) References Cited

U.S. PATENT DOCUMENTS

| | | | |
|---|---|---|---|
| 4,910,148 A | 3/1990 | Sorensen et al. | |
| 5,700,959 A | 12/1997 | Homberg | |
| 6,096,554 A | 8/2000 | Tajima et al. | |
| 6,409,925 B1 | 6/2002 | Gombinsky | |
| 6,679,375 B1* | 1/2004 | Coory | ........................ 206/219 |
| 6,776,174 B2* | 8/2004 | Nisson | ................ B01L 3/5085 134/104.4 |
| 7,704,734 B2 | 4/2010 | Bader | |
| 2001/0024821 A1* | 9/2001 | Potter | .................... C12M 23/10 435/297.5 |
| 2003/0082565 A1* | 5/2003 | Jang | ................................ 435/6 |
| 2004/0009641 A1 | 1/2004 | Ahn et al. | |
| 2004/0067596 A1* | 4/2004 | Halverson | ............. B01L 3/5027 436/180 |
| 2004/0157224 A1 | 8/2004 | Roh et al. | |
| 2004/0166577 A1 | 8/2004 | Storek et al. | |
| 2005/0054101 A1 | 3/2005 | Felder | |
| 2005/0084954 A1* | 4/2005 | Bader | .................... C12M 35/04 435/295.1 |
| 2006/0021673 A1* | 2/2006 | Rodewald | ............. B65B 7/2835 141/127 |
| 2006/0063252 A1 | 3/2006 | Ito et al. | |
| 2006/0081539 A1 | 4/2006 | Safar et al. | |
| 2006/0121606 A1* | 6/2006 | Ito | ......................... C12N 5/0062 435/325 |
| 2006/0204997 A1* | 9/2006 | Macioszek | ........... C12Q 1/6851 435/6.11 |
| 2006/0252054 A1 | 11/2006 | Lin et al. | |
| 2008/0023388 A1* | 1/2008 | Cho | ................... B01L 3/502761 210/222 |
| 2009/0064800 A1* | 3/2009 | Fasching | ................. B01L 9/523 73/863.21 |
| 2009/0137018 A1 | 5/2009 | Becker et al. | |
| 2009/0220979 A1* | 9/2009 | Davis et al. | ....................... 435/6 |
| 2009/0324451 A1* | 12/2009 | Yin | ......................... B01L 9/523 422/400 |

FOREIGN PATENT DOCUMENTS

| | | | |
|---|---|---|---|
| JP | 2005312386 | 11/2005 | |
| WO | 95/00247 | 1/1995 | |
| WO | 2004083412 | 9/2004 | |
| WO | 2004083416 | 9/2004 | |
| WO | 2005003332 | 1/2005 | |
| WO | 2005010162 | 3/2005 | |
| WO | WO-2007116594 A1 * | 10/2007 | ............ C12N 5/0697 |
| WO | WO-2008048027 A1 * | 4/2008 | ............ C12M 47/04 |
| WO | WO 2009076560 A2 * | 6/2009 | ....... G01N 33/54333 |
| WO | 2010036957 | 4/2010 | |
| WO | WO 2010036957 A1 * | 4/2010 | |
| WO | PCT/US2011/046183 | 9/2012 | |

OTHER PUBLICATIONS

Lee Jong-Kook, English-machine translation of WO2007/116594A1. (Year: 2007).*

Akira Ito, English-machine translation of JP 2004-254519A. (Year: 2004).*

Ito, et al., Medical Application of Functionalized Magnetic Nanoparticles, Journal of Bioscience and Bioengineering 100(1): 1-11 (2005).

Souza G. R. et al. Three-dimensional Tissue Culture Based on Magnetic Cell Leviation. Nature Nanotechnol. 5, 291-296, doi:10.1038/nnano.2010.23 (2010)).

* cited by examiner

HARDWARE FOR MAGNETIC 3D CULTURE

PRIOR RELATED APPLICATIONS

This application is a continuation of International Application Number PCT/US11/46183, filed Aug. 2, 2011, which claims priority to U.S. Ser. No. 61/372,164, filed Aug. 10, 2010 Both applications are incorporated by reference in their entirety.

FEDERALLY SPONSORED RESEARCH STATEMENT

Not applicable.

REFERENCE TO MICROFICHE APPENDIX

Not applicable.

FIELD OF THE INVENTION

The invention relates to various devices for manipulating magnetic cells that have magnetic particles in them or attached to them, which is important in biological research and applications. More particularly, the invention relates to simple, durable and inexpensive vessels for culturing magnetic cells and a magnetic pipettor for moving magnetic cells.

BACKGROUND OF THE INVENTION

Cell culturing, which is the growth of cells in an artificial in vitro environment, is a crucial technique in life science research and development and many biotechnology and health applications. An ideal cell culturing environment is one that promotes fast and robust growth of healthy cells, wherein the cell morphology and function are dominated by cell-cell interactions, cell-specific signaling, and/or experimental control variables, rather than being influenced by the properties of the artificial culturing environment. Often, it is desirable to grow cells that closely resemble cells grown in living organisms, including their gene expression, functional characteristics of differentiated cells, and the formation of an extracellular matrix. Cost and scalability of production are also critical considerations for the application potential of such technologies.

As interest in nanotechnology, materials, and cellular biology has grown, it has become evident that an important limitation in our ability to manipulate, grow and use cells and tissues has been our lack of ability to control the pattern of cells and tissues useful for cellular biology and medicine.

During development of living organisms, structure and order in the form of patterns naturally emerge through mechanisms that are still not fully understood. If one wants to study or replicate living tissue in an artificial environment, it is critical to be able to reproduce the naturally existing patterns. The ability to engineer and manually control the patterns of living cells, especially in three-dimensions and on surfaces, will enable many bioengineering and medical applications heretofore not realized.

Traditional cell culturing in Petri dishes produces two-dimensional (2D) cell growth with gene expression, signaling, and morphology that can differ significantly from conditions in 3D living organisms, and thus compromising the clinical relevancy of the cells or tissue for medical use.

While rotating bioreactors or protein-based gel environments have been developed in attempts to allow three-dimensional (3D) cell culturing, broad application of such methods has been severely hampered by high-cost or complexity. Thus, a platform technology to enable 3D cell culturing is still an unmet need.

Furthermore, as the use of cultured cells continue to develop, it is increasingly difficult to develop systems for safely manipulating and handling these entities. For example, regulatory agencies and good laboratory practices often attempt to minimize the amount of exposure of cells to external objects, so as to minimize contamination. Thus, devices which can manipulate cells and tissue without exposure to external environment is desirable.

A recent development in 3D cell culturing techniques is to use magnetic forces on cells or on magnetic microcarriers coated with cells, to create three dimensional cell cultures (e.g., Akira in US2006063252, WO2004083412, WO2004083416; Becker in US2009137018, WO2005003332; Felder in US2005054101, WO2005010162; Souza in WO2010036957; Ito, et al., Medical Application of Functionalized Magnetic Nanoparticles, JOURNAL OF BIOSCIENCE AND BIOENGINEERING 100(1): 1-11 (2005); and Souza, G. R. et al. Three-dimensional Tissue Culture Based on Magnetic Cell Levitation. Nature Nanotechnol. 5, 291-296, doi:10.1038/nnano.2010.23 (2010)).

The current state of the art in magnetic culturing devices is the simple magnet on top of a Petri dish used by Souza in WO2010036957 and Souza, et al. Three-dimensional Tissue Culture Based on Magnetic Cell Levitation. Nature Nanotechnol. 5, 291-296, doi:10.1038/nnano.2010.23 (2010). While, simple and at least effective in principle, such devices are not amenable to scale up, are easily dislodged, and do not allow for complex manipulations of culture conditions or magnetic cells.

Ito, et al., Medical Application of Functionalized Magnetic Nanoparticles, Journal of Bioscience and Bioengineering 100(1): 1-11 (2005), and US2006063252, WO2004083412, WO2004083416 merely use a neodymium magnet placed outside the bottom of the well. Like the magnet on a lid, these are not amenable to scale up, are easily dislodged, and do not allow for complex manipulations of culture conditions.

US2005054101 and WO2005010162 describes a machine for holding and moving magnets to move, position, and agitate magnetic microcarriers and attached cells. However, this device is not compatible with microscopy tools, and it requires a stand-alone complex device. Neither does it provide easy access to the levitated cultures, thus making it difficult to manipulate the cultures. Furthermore, cells have to be first attached to the surface of microcarriers, which are several times larger than a single cell. This introduces an artificial substrate with which cells interact, rather than rapidly promoting natural cell-cell interactions. The magnetic fields and field gradients produced by this arrangement are also relatively weak and require cells to be attached to large microcarriers containing a large amount of magnetic material in order to manipulate them.

US2009137018 and WO2005003332 described a static arrangement of magnets for levitation of microcarriers. This device is cumbersome however, and not suitable for scale up. Also, this device requires cells to be placed in a bag and a large magnet is above or around the large plastic bag. Thus, the device is not compatible with microscopy tools. Neither does it provide easy access to the levitated cultures, making it difficult to manipulate the cultures. Furthermore, again the cells are first attached to the surface of the microcarriers, which as discussed above introduces an artificial substrate into the culture. The magnetic fields and field gradients produced by this arrangement are also relatively weak and require cells to be attached to large microcarriers containing a large amount of magnetic material in order to manipulate them.

To make 3D cell culturing with magnetic forces more convenient, flexible, and safer for users, there is a great need for improving the methods and hardware to hold magnets in the proper orientation with respect to the cells and container in which they are contained. There is also a great need for methods and hardware for manipulating the magnets and cells during and after culturing. In many cases it would be advantageous to have such systems be compatible with commonly used cell culturing vessels like flasks and Petri dishes, multi-well plates, and high-throughput culturing systems.

Thus, what is needed in the art are magnetic culture devices and magnetic pipettes that can be used with existing robotics and microtiter or Petri plates, and that are simple, robust, easily scaled up and inexpensive. Further, the devices should be tunable for the application of interest. Thus, ideally the magnetic field shape or intensity can be easily varied in a manner that is simple, convenient, reproducible and consistent with sterile cell culture techniques.

SUMMARY OF THE INVENTION

The present invention relates to devices for holding magnets in a proper orientation with respect to vessels for 3D cell culturing of magnetized cells, either as a component of the vessel, or a separate component working with the vessel. The present invention also relates to magnetic pipettes for manipulating those magnetic cells.

As used herein "vessel" or "well" refers to any container for culturing cells, such as a Petri dish, flask, or multiwell culturing plate.

"Magnet" refers to any material creating a magnetic field and can be a permanent magnet or an electromagnet.

The devices are designed to position magnets at an appropriate distance from cells and from neighboring magnets (when neighboring magnets are present) to create the necessary magnetic field profiles to levitate and/or manipulate cells and to hold the magnets in place during use. The devices also improve safety and ease of use of magnets by keeping them aligned and keeping them from colliding.

Capabilities to move the magnets are incorporated into the design in some realizations of the invention, which enable the directed manipulation of tissue grown from cells containing or attached to magnetic material. Thus, in some embodiments the height of the magnets and horizontal position of the magnets on cell culture vessels is easily adjusted. In some cases, the devices of the invention are designed to be compatible with commonly used cell culturing vessels like flasks and Petri dishes, multi-well plates, and high-throughput culturing systems.

The magnetic pipettor of the invention consists of a pen- or pipette-like mechanism, wherein cells are picked up into a sterile chamber or on a sterile surface by virtue of a magnetic field created by a magnet in the pen. A simple switch moves the magnet far enough away from the cell to allow them to be deposited in another location. The switch can be similar in mechanism to a retractable ball point pen, or even more simply, the magnet can be simply lifted out of the pen-like device (and/or the field direction reversed). Thus, the cells (or tissue) can easily and gently be lifted and placed according to need in a sterile manner. Multipipettors are also provided. In yet another embodiment, the magnet is an electromagnet and a simple battery or other power source and circuitry control both the field strength and its directionality.

Preferably however, the magnet is a permanent magnet and has a field strength of about 0.001-2 Tesla. However, the strength is inversely proportional to the cube of the distance from the magnetic source, and thus the required field strength can vary depending upon the distance from magnet to the cell culture. In those embodiments where multiple magnets are used in arrays, there will be some interaction with neighboring magnetic fields, and thus some optimization of placement may be needed for the application and cell type.

The magnet can be any shape needed to affect the required growth patterns. For example, it may be possible to grow tubes, useful for example in growing veins and arteries, with a washer-shaped (annular) magnet that establishes a magnetic field with a hole in the center.

Preferably, a rare earth magnet is employed. Examples of rare earth magnets suitable for use with the present invention include, but are not limited to, neodymium rare earth magnets, samarium-cobalt rare earth magnets, $Nd_2Fe_{14}B$, $SmCo_5$, $Sm(Co,Fe,Cu,Zr)_7$, $YCO_5$, or any combination thereof.

Neodymium rare earth magnets are the strongest and most affordable type of permanent magnet, and are generally preferred, but samarium-cobalt magnets have a higher Curie temperature (the temperature at which the material loses its magnetism) and may be preferred for uses involving high sterilization temperatures.

Particular types of rare earth magnets may also be selected as desired according to the conditions to which the rare earth magnets may be exposed. For example, any of the following factors may be considered in selecting a type of rare earth magnet: remanence (Br) (which measures the strength of the magnetic field), coercivity (Hci) (the material's resistance to becoming demagnetized), energy product (BHmax) (the density of magnetic energy), and the Curie temperature (Tc). Generally, rare earth magnets have higher remanence, much higher coercivity and energy product than other types of magnets. Where high magnetic anisotropy is desired, $YCO_5$ may be suitable for use.

In place of or in addition to the rare earth magnets, powered magnets may be incorporated into the devices of the invention, and batteries may be used to power the powered magnets as desired. Alternatively, RF or other electromagnetic radiation activated power sources can be used to power the magnet, such as is used with RFID tags. However, for simplicity, durability, and cost reasons, the permanent magnet is preferred.

We have tested a number of magnets, both in modeling studies and in real experiments, and can elaborate a number of principals for the selection of magnetic size, strength and shape. Firstly, the magnet size is confined by the size of the plates with which it will be used, as excess magnet is a waste of resources. Further, if the magnets are designed to fit inside the plate, without the use of an intervening plate cover, then the magnet must also fit inside each well of the plate, preferably without touching the well. Second, the height of the magnet can vary with increasing field strength, stronger magnets being held farther away than weak magnets, and generally the magnets being positioned so as to not touch the media or the cover (if used). These considerations must be balanced against the magnet's lifting height of the magnet (how far away the magnet can be and still lift cells), as well as the desired growing height. Magnetic field interference is also important in designing multi-magnet holders. Additionally, meniscus effects from the media surface shape become increasingly important in plates with increasing well number.

We tested candidate magnets for a 35 mm plate that included various disc magnets from K&J MAGNETICS®. Magnet MM-A-32 and MM-A-20 resulted in desirable levitation results when used for 35 mm petri plates. MM-A-32 is an annular shaped magnet of 1.26" (32 mm)×0.32" (8 mm) with a small tapered countersunk central hole 0.22-0.39". It is a Grade 38 NdFeB magnet with Ni—Cu—Ni coating, axial poles, a pull force of 55.1 lbs, Br max of 12,600 Gauss and BH max of 38 MGOe. MM-A-20 is very similar, 0.79"×0.28", hole 0.18-0.33", but due to its smaller size having a pull force of only 13.20 lbs, Br max of 12,600 Gauss, and BH max of 38 MGOe. The same magnets can be used for a standard six well plate (127.76 mm×85.47 mm, wells are 35.43 mm×17.4 mm). D42-N52, D46-N52, D48-N52 resulted in desirable levitation for a 24 well plate.

We also tested candidate magnets for a typical 96 well plate that includes D22-N52, D23, and D24-N50 from K&J MAGNETICS®. Our results indicate that the gradient and field strength produced by each permanent magnet are important considerations, and that a steep gradient and high field strength serve to minimize interference between magnets and still provide good lifting and growing heights. In our experiments, we found that D22-N52 has the steepest gradient and produces forces comparable to MM-A-20 and MM-A-32 and is a good choice for a 96 well magnet holder. D22-N52 is a disc shape magnet (no hole) of ⅛×⅛ inches, and has a pull force of 0.84-1.05 lbs. The surface field is 6619 Gauss, the Br max is 14,800 Gauss, and the BH max is 52 MGOe.

Finally, the shape of the magnet can be varied to influence the shape of the growing 3D culture. For example, annular magnets can lead to annular cultures (that can be stacked to form tubes), and long magnets can lead to 3D cultures that are longer than wide.

BRIEF DESCRIPTION OF THE DRAWINGS

FIG. 7A-B. Schematic of spring-loaded magnetic cell pipettor. FIG. 7A. Showing pipettor in use.

FIG. 9. A. Fiber-optic coupled to magnetic cell pipettor. B. Cross section of A.

DESCRIPTION OF EMBODIMENTS OF THE INVENTION

Generally speaking the invention relates to a magnetic cell culture plate comprising at least one well having a matching cap fitting over (or under) said well, at least one of said well or said cap being having a magnet affixed to said well or cap. Alternatively, the invention can comprise just the cap with attached magnet, herein called a magnetic cap or holder or drive, which is sized to fit a culture vessel. Generally, the magnet is affixed to said cap with adhesives, fasteners or is snap fit with a receptacle designed to accept a magnet, such as a snap fit receptacle.

The magnetic cap can be used either above or below the vessel, and if used above can lie either over the normal vessel cover or if sterilized and without apertures can replace the cover.

In preferred embodiments, the cap is adjustable so as to adjust the height of said magnet from the vessel. In other embodiments, the position of the magnet on the cap is also adjustable. In one embodiment, the cap has an adjustable collar that fits outside or inside the cap and which is fitted with grooves or ridges that match ridges or grooves on the cap, so that unscrewing the collar has the effect of increasing the height of the cap. Instead of using a collar, the cap can also be fitted with screws or other protrusions that can be lengthened, thus having the same effect. This would allow even a square cap to be easily adjustable.

The cap can also be sized and shaped to fit a multiwell plate. Thus, the invention can comprise a magnetic cell culture plate, comprising a plurality of wells in an array, a cap covering said plurality of wells, and a plurality of magnets in an array affixed to said cap, such that each well, or each well in a subset of the wells, has a magnet over said well when said cap is in place over said plurality of wells. As above, the invention can comprise just the cap and magnets, which can be used with commercially available plate ware, and the cap height can be adjustable.

In some embodiments, the cap is merely a plate cover with holes drilled or injection molded therein over each well, and a separate plate having magnetic pins is provided to fit to the cap, the magnets protruding through the hole to varying degrees. In this embodiment, a number of separate plates with magnetic of different lengths or strengths can be provided, again providing the user with an easily customizable magnetic 3D culture hardware. As above, this plate cap can be used above or below a cell culture vessel.

In yet another embodiment, the cap or drive has a lip to prevent it from being easily dislodged from the plate or plate cover, and has depressions thereon to receive one or more magnets. Preferably, the magnets are snap fit into these depressions, allowing magnets to be switched out for different magnets strengths or shapes. If different magnet shapes are used, the invention can also provide an adaptor for each shape, thus allowing the magnets to be snap fit into the adaptor, and then snap fit into the drive. In other embodiments, the magnets are more or less permanently affixed, by e.g., an adhesive.

Yet another embodiment of the invention is a magnetic pipettor that comprises a magnet inside a housing, over which an overcap fits, thus separating the magnet from the cells. The overcap can be an inert, sterilizable material or can be coated with agents (e.g., collagen or BSA) as needed for the particular use. The housing also contains means for adjusting either magnet height or polarity so that magnetic cells can be lifted or set down, as needed. In preferred embodiments such means is just a spring or other biasing mechanism, and detents for catching the magnet and holding it either close or far from the tip of the overcap. In this regard, ballpoint pens and pipettors can easily be adapted for such use, and the patent literature describing same provides many possible mechanisms for manufacturing such a device.

In embodiments that employ electromagnets, the polarity is easily reversed with conventional circuitry, however the simple ball point pen-like adjustor may be preferred due to low cost. The pen can be unitary, or can comprise multiple tips and magnets, as in a multi-pipettor, and can comprise optional elements such as light source, means for air volume displacement, and the like.

In preferred embodiments, the cap (protruding surface) is a single use disposable cap, like a pipette tip, but shaped so as to be appropriate for the transfer of large 3D cultures, and the cap snap fits or pressure fits on the outer surface of the pipettor tip. The cap can be flat bottomed, or flared or cup shaped so as to allow the transfer of larger cultures, and a variety of caps can be made for use with cultures of different sizes.

Eventually, the culture will become too large to transfer by surface tension effects, even with a flared cap, and it may be desirable to have a device that slips under the cells for transfer, e.g., like a magnetic spoon, wherein the protruding surface slips under the cells, and the magnet is placed on a flexible cables, and can still slide into the horizontal protruding surface and securely attract and position the culture.

EXAMPLE 1: SINGLE WELL CAP MAGNET HOLDER

Referring now to the invention in more detail, in FIG. 1 and FIG. 2 there is shown a magnetic holder that fits on the top or the bottom of a single well cell culture dish. In detail FIG. 1A shows a magnetic holder 1 with a magnet 2 affixed to it. The prototype magnetic holder or drive 1 was made of acrylic, but any polymer, resin, ceramic, glass or metal can be used. Inexpensive polymers such as acrylate or polycarbonate are preferred as durable, inexpensive, sterilizable, and transparent, which allows visualization of contents.

Figure 1A:
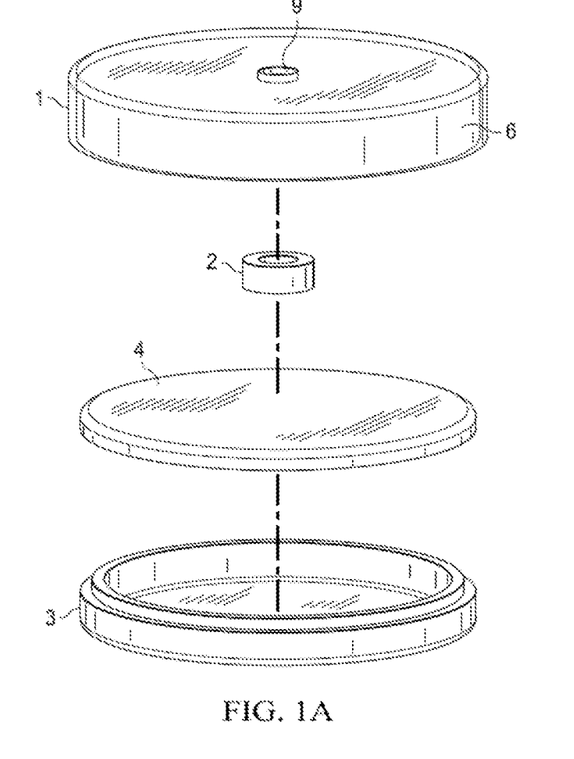
FIG. 1A-E. A. Exploded view of single-well magnet drive with magnet and culture plate and lid. B. Assembled magnet drive in place under a typical petri plate. C. Three single well plates in a row showing the intra-magnet distance -I-. D. A six well magnet holder and standard 6 well plate. E. 24 well magnet with specially designed lid also having wells designed to fit the magnets and then fit inside the wells of the plate, thus allowing very close positioning of the magnets.

In this instance, the magnetic holder 1 has a hole 9 through which one can visualize the contents of the plate if an annular magnet 2 is used. The magnetic holder 1 can sit over a petri plate 3 with lid or cover 4, or can sit under it, depending on the application and/or magnet orientation.

A circular or disc shaped magnetic drive 1 is shown in FIG. 1, but it could be rectangular, triangular, hexagonal, or any other shape. The preferred shapes are compatible with existing cell culture plates and flasks. We have shown the magnet centered on the cap, but it does not have to be.

The magnetic holder 1 can be used alone, or can be laid over the existing vessel caps 4 as shown herein. An optional aperture 9 can be included in the holder 1 to facilitate imaging the cultures if needed.

The size of this cap will vary depending on the size and shape of the tissue culture vessel and the size and strength of the magnetic field resulting from the magnet being held. As an example, the size of the cap can vary from 5 mm to 100 mm in outer diameter. If this device is to be used to culture large amounts of cells (such as cultures starting with more than 50M cells per vessel), this may require larger magnets, therefore holders could vary in size and shape.

Examples of applications requiring large-scale culture would be the production of recombinant proteins, production of extra-cellular matrix proteins, activation of T-cell by antigen presenting proteins. The height of this cap is a function of magnet strength. Stronger magnets may require taller holders.

The magnet 2 can be cylindrical or disc shaped, ring or washer shaped, square, triangular and the like, but is not limited to these shapes. Here we show a washer shaped magnet 2 with a small hole therein to allow visualization of the culture below.

The size of the magnet will vary according to the application. Example of size is 32 mm in outer diameter and 6 mm in height. This size could very form 2 mm to 100 mm, but the sizes are not limited. A combination of magnets magnetically held together can also be used.

Figure 1B:
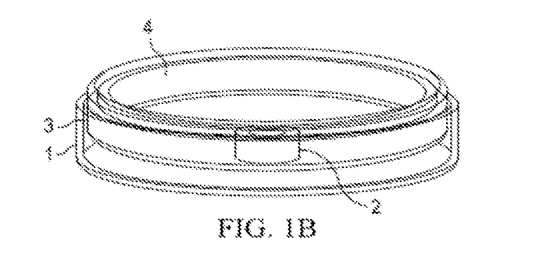
Figure 1C:
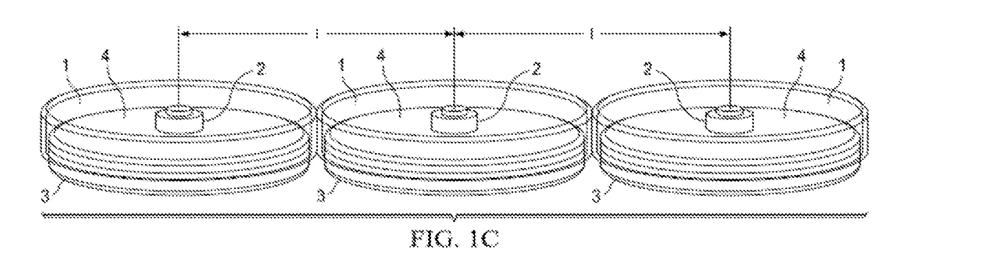

FIG. 1B shows the magnet holder 1 assembled with magnet 2 in the center, and in this instance mounted under Petri dish 3, which is covered with the petri cover 4. FIG. 1C shows three such Petri plates 3 side by side, but with magnetic holder 1 on top of the Petri cover 4. The minimum distance -1- between the center of magnet holders is defined by the holder size and magnetic strength of magnets, and should be such that the fields do not unduly interfere.

The magnet 2 can be held in place on the holder 1 with an adhesive or more preferably, the holder 1 has a fitting into which the magnet 2 can be snap fit. It can also be held in place with any convention fasteners such as screws and the like. Screws or snap fits may be preferred where the magnets 2 are expected to exchangeable and thus allow easy variation of shape, size and strength.

The magnetic holder 1 also keeps the magnet from random displacement relative to the tissue culture dish due to the lip or edge 6, which fits over the culture plate. In summary, the magnet holder will keep the magnet in place (either on top or at the bottom) relative to the tissue culture flask or Petri plate.

The distance between magnets -1- should be defined relative to the size and shape of the tissue culture flask and/or the strength of the magnet. Stronger magnets will require larger distances to keep neighboring magnets from disturbing their respective levitated cultures and/or interacting with each other in a manner that can cause them to be displaced from the top or bottom of the tissue culture dish. This is also important for safety reasons, to prevent fingers from being trapped between very strong magnets, and avoid cross contamination between samples if magnets are displaced and culture media spilled, and/or sample lost.

The use of the magnetic drive 1 is not limited to top of the culture plates, but it could also be placed at the bottom of well. When at the bottom, the magnet holder provides increased stability.

Figure 1D:
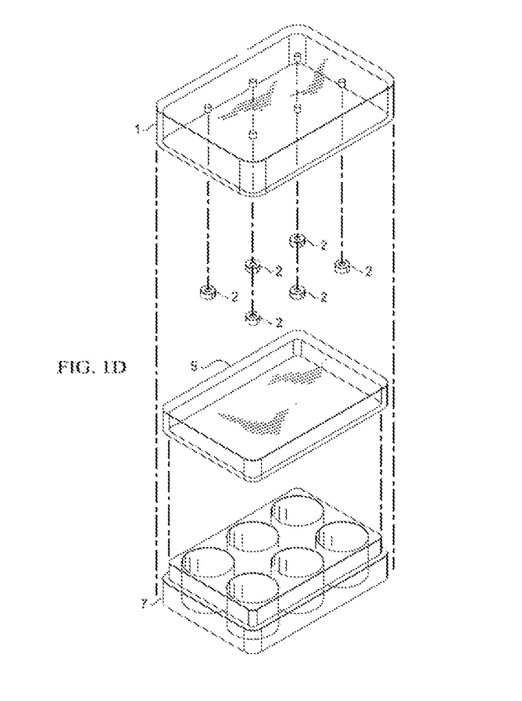

FIG. 1D shows a 6 well magnetic holder 1 with six magnets 2 designed to fit over (or under) a six well plate 7 and cover 6. We have shown the magnets 2 here placed underneath the cover, but we have also made a prototype device where the magnets fit into depressions of the surface of the magnetic holder, and where each depression also has a viewing hole. The magnetic holder 1 can have a lip or edge to hold the device in place over a plate as shown here, or can be a flat surface lacking any protruding lip on the underside, as in our first prototype. However, this is less stable and a lip is preferred.

Figure 1E:
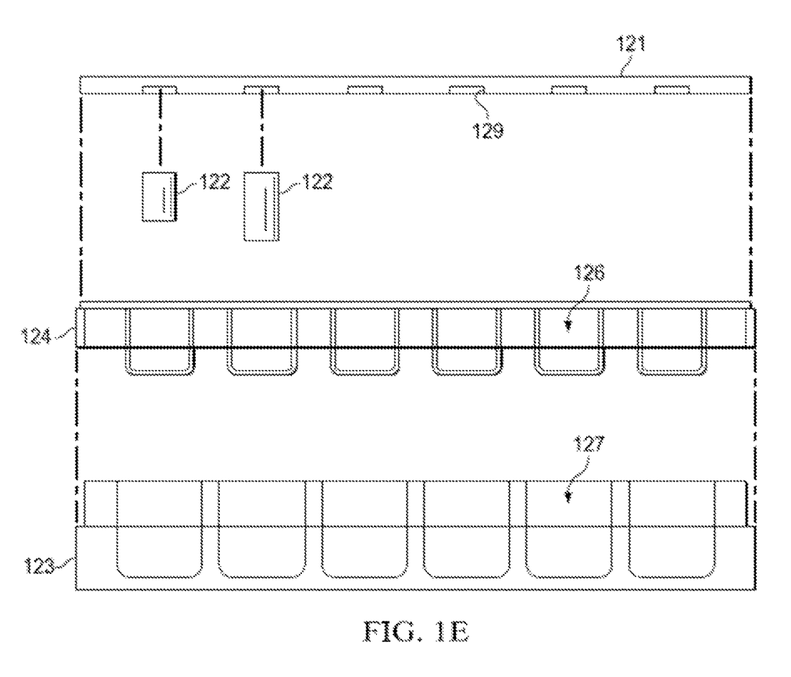

FIG. 1E shows a 24-well plate model wherein both the magnetic drive and a special lid are made to fit either over existing plates or a plate and lid combination will both be made. The magnetic drive 121 will be similar to that already described with magnets 122 placed in an array on the drive or holder 121, which has an array of recesses 129 to receive the magnets 122. Epoxy fixative will then be used to glue 24 ring magnets 122 into the cavities 129 on the drive, thus completing levitator assembly and forming the 24-well magnetic drive. This will be used with a culture plate 123 and a specially designed lid 124 having 24 wells 126 fitted to receive the magnets and fit inside the 24 wells of the plate 127. In this way, the magnets can be brought closer to the culture, thus levitating cells, and smaller magnets can be used, thus minimizing interference magnetic fields from neighboring wells.

The special lid can be pre-sterilized and thus preserve the sterility of the system. This will allow the magnet drives to be reusable, while the lid will be disposable or designed for single use. The magnetic drive and special lid concept in FIG. 1E can be adapted with standard or specially designed multiwell plates with 6, 12, 24, 48, 96, 384 and/or 1536 wells.

Figure 2A:
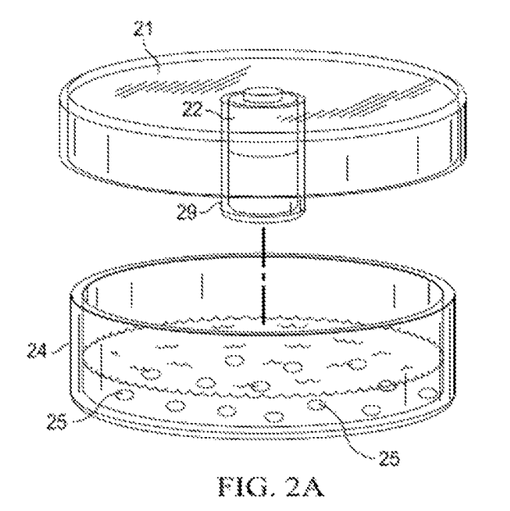
FIG. 2A-C. A. Magnet holder cap modified with protruding surface for collecting cells levitating cells. B. The protruding surface can reach the media in the petri plate, thus collecting the cells for transfer, e.g., to another plate. C. Magnet holder cap with protruding surface carrying magnetized cells.
Figure 2B:
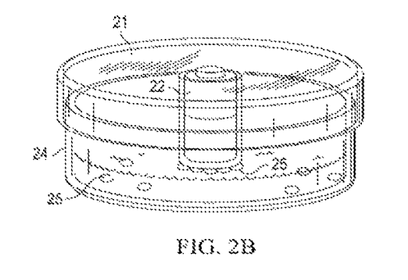
Figure 2C:
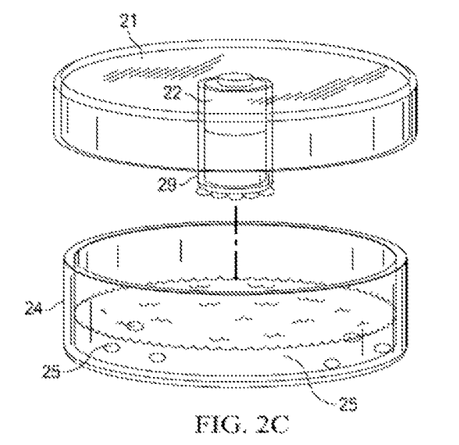

In FIG. 2A there is shown a magnet holder 21 modified with protruding surface 29 for collecting levitating cells. In this embodiment, the magnet is placed inside a cap-shaped protruding surface (but the surface can be any shape), such that only this surface contacts media when in use. Tissue culture vessel 24 is shown with cells 25 on the bottom. In FIG. 2B, the holder is moved close enough to the plate 24 so that cells 25 are collected on the protruding surface 29 by attraction to the magnet 22. Once attached to the immersed surface, the cells can be easily removed from solution as in FIG. 2C. The attached cells can then be counted, separated between levitating and non-levitating cells. The surface attached cells can also be used for analysis, culturing in different flask by displacing the magnet, washing cells off with media or trypsinizing the cells. Furthermore, the device can be used to separate, sort, transfer, and evaluate yield of magnetized cells. It is possible to make this protruding surface snap or pressure fit to an protruding edge (not shown) on the drive, thus allowing single use, pre-sterilized surface to be prepared and snap fit onto the drive when needed, in the same way that a pipette tip if pressed onto a pipettor. In this embodiment, a simple means for ejecting the cap can also be provided.

FIGS. 3 and 4 show multiwell magnet assembly for culturing multiple samples by magnetic levitation. The components of FIG. 3 are a multiwell magnetic drive 31 with an array of magnets 32 protruding therefrom. In more detail, this multiwell magnet holder was made of acrylic or polycarbonate wherein a number of holes were drilled and magnets were inserted therein. In this instance, the magnets were held by either an adhesive or by friction inside a metal holder, heat welding, snap fit, fasteners or any other means can be used to secure the magnets.

The multiwall magnetic holder 31 can be used with standard or specially designed multiwell plates 33 with 6, 12, 24, 48, 96, 384 and/or 1536 wells 34. We have shown magnet protruding down into the wells in the multiwall case, and the magnetic holder 31 is used without a plate cover because at some point, the magnets must get close enough to the cells 35 so as to levitate same, but avoid interference effects between well. In other cases the magnets 32 can be sized so as to not protrude into the well, and the device can be combined with a plate magnet 36, as shown in FIG. 3B. In such case, the magnetic holder 31 could still be used with a plate cover (not shown). Once cells reach the meniscus of the media and the smaller magnets 32 have the strength to sustain levitation, this large plate magnet 36 could be removed.

Figure 3A:
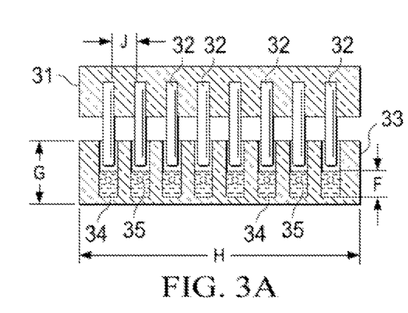
FIG. 3A-B. A. Multi-magnet holder for 96 well tissue culture plate. This embodiment is intended to be used with only the bottom of a 96 well plate (not the cover), allowing the magnets to get closer to the cells. B. Same plate, but with an additional plate magnet placed on top to further increase field strength. In such an embodiment, the plate could be used with its cover (not shown) because of the extra field strength provided by the plate magnet.
Figure 3B:
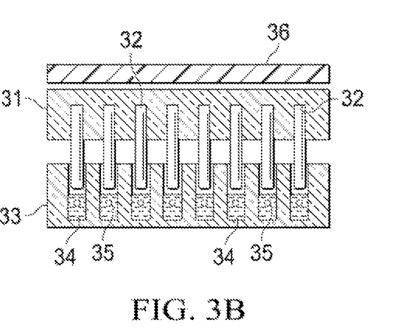

Also shown in FIG. 3A is -G-, which is the height of the microwell plate 33. This height will vary depending on the application and/or magnetic strength of magnets being used. Shorter plates of approximately 2.5 mm in height, but not limited to it, would be optimum for higher throughput applications, such as when using 96, 384, and 1536 plates. The length of multiwell plate is -H- and the depth of the media is -F-.

Magnets may protrude inside each well to get close enough to the cells to provide the needed magnetic field to levitate cells. With stronger magnets, the magnet can be completely above the wells, and even above the sterile well cover or lid. In some embodiments, these devices could consist of 6, 12, 24, 48, 96, 384, 1536 magnets, or any number in between.

Figure 4A:
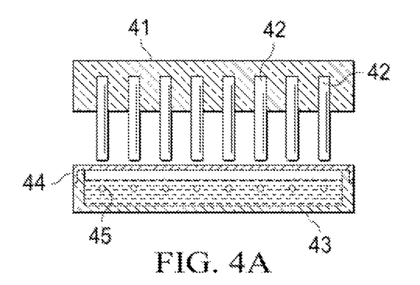
FIG. 4A-B. Multi-magnet holder for culturing vessel without individual wells (or with one large well). The magnets can either penetrate into the plate, as shown in FIG. 3, or not as shown in FIG. 4A, depending on field strength. If needed, an additional plate magnet can be used, as shown in FIG. 4B.
Figure 4B:
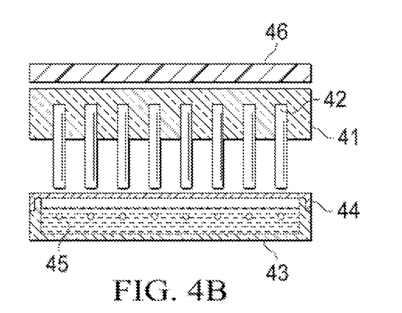

The magnetic holder described in FIG. 3 does not have to be used with plates having multi wells, but can be used with fewer well or even a single well as shown in FIG. 4A wherein the magnetic holder 41 with magnets 42 is used for a large Petri plate or culture dish 43 with lid 44 to levitate cells 45. If needed, the device can also be used with a plate magnet 46 to increase field strength, as shown in FIG. 4B. Magnets 42 can also be removed as needed to fit, e.g., a six well plate. Thus, the device is not limited in use to a plate having the same number of wells as there are magnets.

The spacing between magnets will initiate/generate individual levitating cultures, which are held in place and separated by the magnetic field. Therefore, this well-less format can be envisioned as an invisible boundary defined by the magnetic field, without internal mechanical barriers, such as found in a multiwell plates. Once the individual cultures grow, they may come in contact with each other, which could be a desirable feature for creating larger cultures with improved nutrient flow because of the spacing between individual cultures. This could also be used to generate multiple spheroid bodies within the same culture media.

We have obtained proof of principle of such a technique based on label-free monitoring of cells cultured with a prototype 6 well magnetic holder, wherein magnets are held in depressions on the top of a flat piece of plastic, wherein each depression also has a viewing hole drilled therethrough. Using the device was as simple as standard 2D techniques, and it was proven to be faster than any other 3D cell culturing product on the market. Cell were treated with Nanoshuttle™ (a proprietary solution from Nano3D Biosciences™, Inc. containing magnetic nanoparticles that allows cells to levitate in a magnetic field) and plated into individual wells using media recommended for their specific cell type. The magnetic drive was immediately placed above the culture and magnetic forces gently levitated and guided cells together to quickly induce cell-cell interactions. The cultures were placed in a standard cell culture incubator and, over time, 3D assemblies formed.

The location of culture assembly can be controlled magnetically. However, the morphology of the assemblies and amount of time needed to reach this stage is cell specific. Some cells types, such as epithelial, form layered sheets and display squamous morphology while others, such as human umbilical vein endothelial cells, display branching structures. Levitated structures can be separated to create multiple samples and viable cells may be removed from the 3D culture for further experimentation. No special additional equipment is required and the magnetic drive is compatible with co-culturing and standard imaging and diagnostic techniques. Cells can be maintained for months and toxins can be introduced into culture and examined for any deleterious effects. Cultures grown with the magnetic drive provide a model of native tissue, which can be exposed to various drugs and monitored for viability.

Figure 5A:
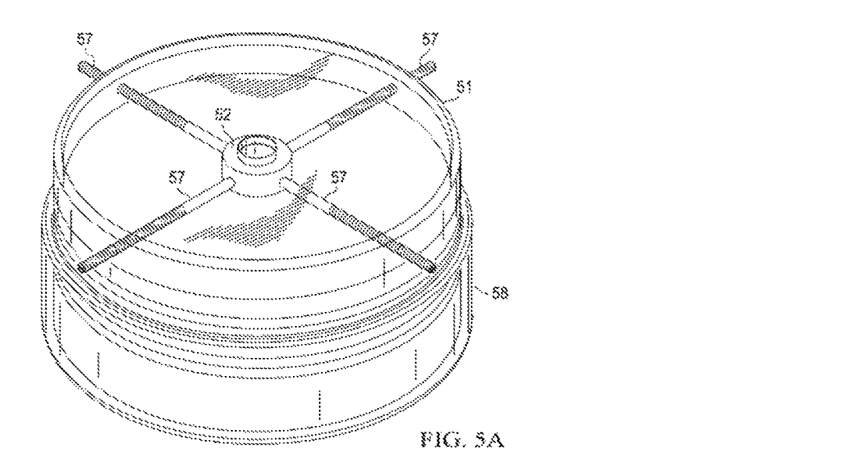
FIG. 5A-B. Adjustable magnet holders. A. Screws allow the magnet to be adjustable in the horizontal plane. The magnet can either sit on top of the holder or on the under side, provided a lip or edge is provided to hold the magnet in place in the vertical axis, yet allow motion in the lateral or horizontal axis. B. A screwable extender allows the magnet to be adjusted in height.
Figure 5B:
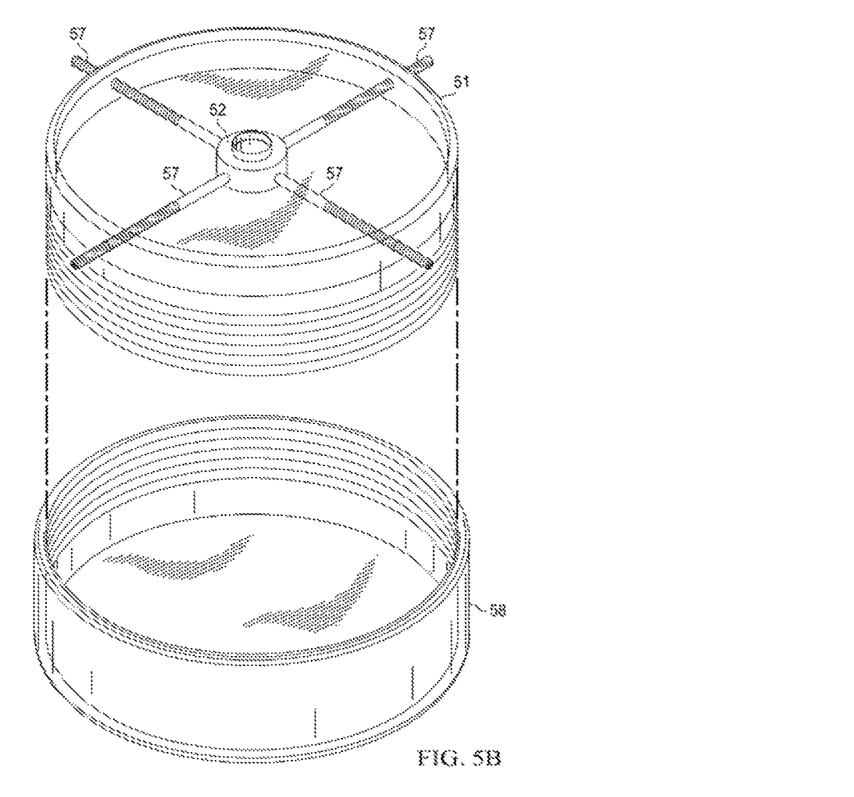

FIGS. 5A-B show the drawings of a holder with adjustable magnet positioning (xyz-axis), such as height, xyz-axis translation (lateral positioning) adjustments of the magnet relative to the tissue culture flask. In detail, the magnetic drive 51 has a magnet 52, and the magnet can be moved around via positioning screws 57. This can also be generalized for a multiwell format and the range of motion may be restricted so that each magnet does not move beyond the range of one well. The height of the magnetic drive can also be adjusted, e.g., by collar 58 with threaded guides for z-axis motion/control.

The xy-axis (horizontal) adjustment may be desirable for translating the magnetized cells sideways. This can be advantageous or useful when cells accumulate under the view path, therefore obstructing a clear image of the levitated cells. This same xy-axis translating action can also be used to disturb the culture.

In FIG. 5 we show a simple mechanical mechanism for displacing the magnet (screw action resulting from threads), however this could be also achieved by electrical (such as, but not limited to, by using solenoids and electric current, electric magnetic), and/magnetic actions. An additional mechanism would be a spring loaded mechanical actions (similar to a light switch) in which a single mechanical motion raises the magnet. This example can also be used to reduce or remove the magnetic field so the levitated structures fall to the bottom of the culture dish and then can be magnetically raised back up.

One of the applications for removing/reducing the magnetic field would be for higher resolution imaging when it is desirable to have the cells at the bottom of the dish closer to imaging objective or elements, such as in the case of confocal microscopy. In more detail, for multiwell designs, it can work with a lever or other mechanical action instead of a screw. This mechanism is also important for transporting the levitating cultures. When transporting the cultures, if a sudden motion occurs that swings/splashes the media and cells so that the media and cells get too close to the magnet, the magnetic force can pull the cells onto the surface just under the magnet. The cells may then adhere to that surface. By lifting the magnet, it prevents the media and cells from getting close enough to the magnet for them to be attracted to and attached to the surface under the magnet.

EXAMPLE 2: MAGNETIC PIPETTOR

FIGS. 6 to 11 show different embodiments of a magnetic pipettor designed to facilitate the manipulation of magnetized cells. This magnetic pen or magnetic pipettor basically includes a non-magnetic surface (such as plastic, glass, metal or Teflon and the like) to prevent cells and/or culture of cells from adhering directly to the magnet, a mechanism for moving the magnet towards or away from this surface to pick up or deposit the cells.

Figure 6A:
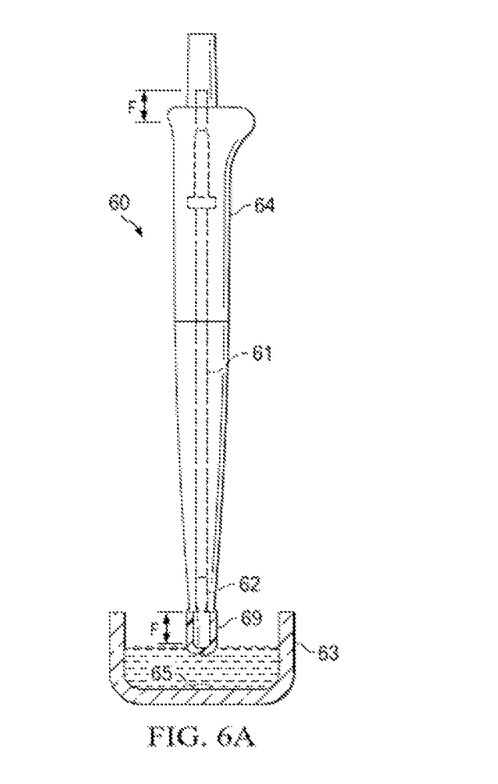
FIG. 6A-B. A. Magnetic pipettor or cell holder. B. Showing the action of the magnetic pipettor.
Figure 6B:
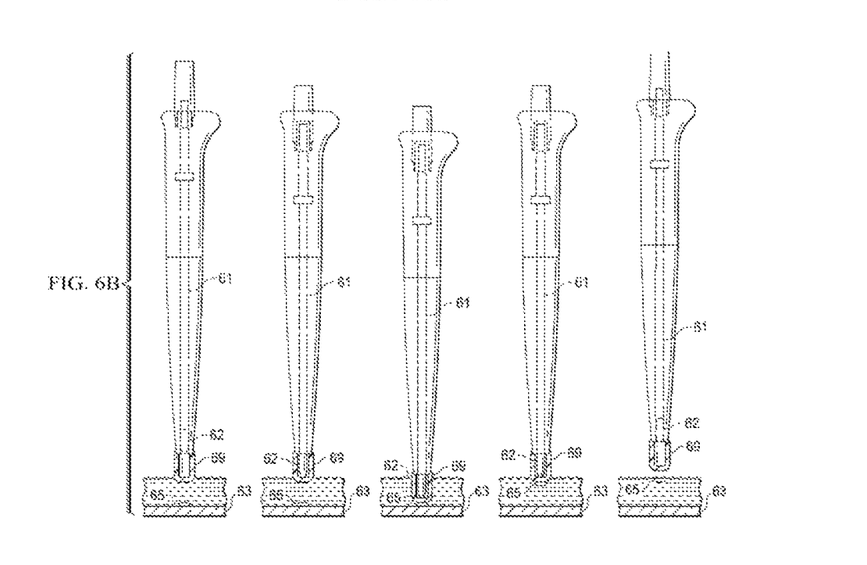

The components of FIGS. 6A-B showing the schematic and pictures of a magnetic pipettor 60 include the guiding structure 61 to hold and move magnet 62. This structure can be a tube, rod, or cable that controls the position and how the magnet 62 slides within the non-adhering and non-magnetic cap 69. The entirety is housed in a suitable housing 64 with needed actuators for raising and lowering the magnet 62 a distance -F-. This guiding structure can be guided manually, mechanically, magnetically, and/or electromagnetically. In preferred embodiment, the magnet is moved in the same way that a retractable ball point pen moves the ink cartridge up and down, using a spring and detents. Prototypes have already been made by converting both a pen and a pipettor to this use, by adding a magnet and a non-adherent cap. By "non-adherent" what is meant is that the cap is made of a material that cells do not quickly bond to, such as those materials used for non-adherent plates. FIG. 6B shows the magnetic pipettor 60 in use picking up a cell 65, which can then be placed anywhere desired.

The magnet 62 can vary in size and shape depending on the application and size and/or shape of multi-well plate. Usually these magnets will consist of cylindrical rings, cylindrical rods, cylindrical disks, and/or square rods, but they are not limited to any particular shape. Smaller magnets can also be stacked for use.

The overcap 69 for keeping the magnet separate from cells is shaped so as to receive and cover the magnet, and is preferably sterilizable and non-adherent. The cap is made of Teflon in our prototype, but any inert, sterilizable material can be used. This cap could also be made of other solid polymers, inert polymers, metals, coated or treated polymers, coated or treated metals, metal treated surfaces, glass or ceramic.

We have shown a flat bottomed overcap 69, but the bottom can also have a depression or well or flared edges so as to pick up additional fluid by capillary action or surface tension. Further, the magnetic pipettor can be combined with a small amount of air displacement as in a normal pipettor, depending on its intended use, but what is shown is a magnetic device that picks up cells by magnetic force, although some surface tension effects will always be present.

Here, we show a cylindrical overcap 69, but this overcap could be of any shape including rectangular, triangular, and hexagonal, and/or any regular or irregular shape. Preferably, the cap mirrors the shape of the tissue culture vessels in cross section and is somewhat smaller than the wells. The overcap can be exchangeable, thus allowing the use of different size caps for different culture plates or different size cultures. The cap can also be disposable, single use, ejectable caps, much like pipette tips, but wherein the pipette tip has been modified to have a closed bottom or tip.

Figure 7A:
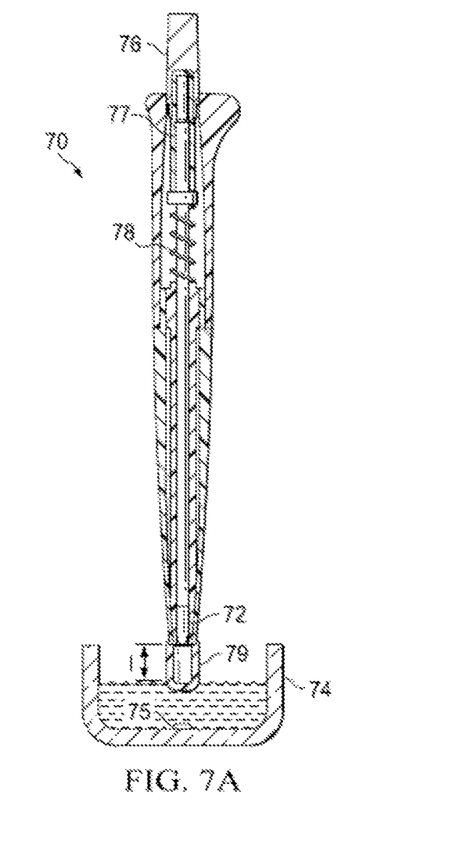
Figure 7B:
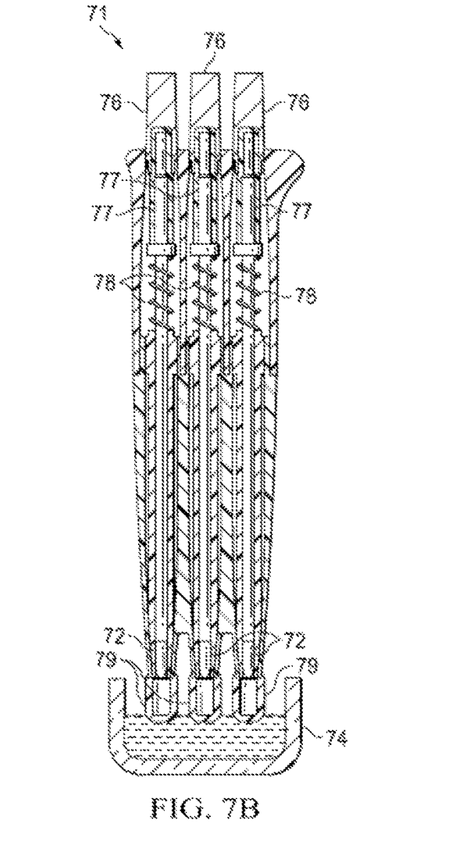
FIG. 7B. Showing multipipettor having three magnetic tips.

FIG. 7 shows a spring-loaded magnetic cell holder 70 with magnet 72, overcap 79, guiding rod 77 attached to magnet 72, push-button 76 for catching or releasing action and spring 78. FIG. 7B shows a multipipettor 71 having three magnetic tips, and FIG. 7A shows the device in use, picking up cell 75 from a culture plate 74.

Figure 8:
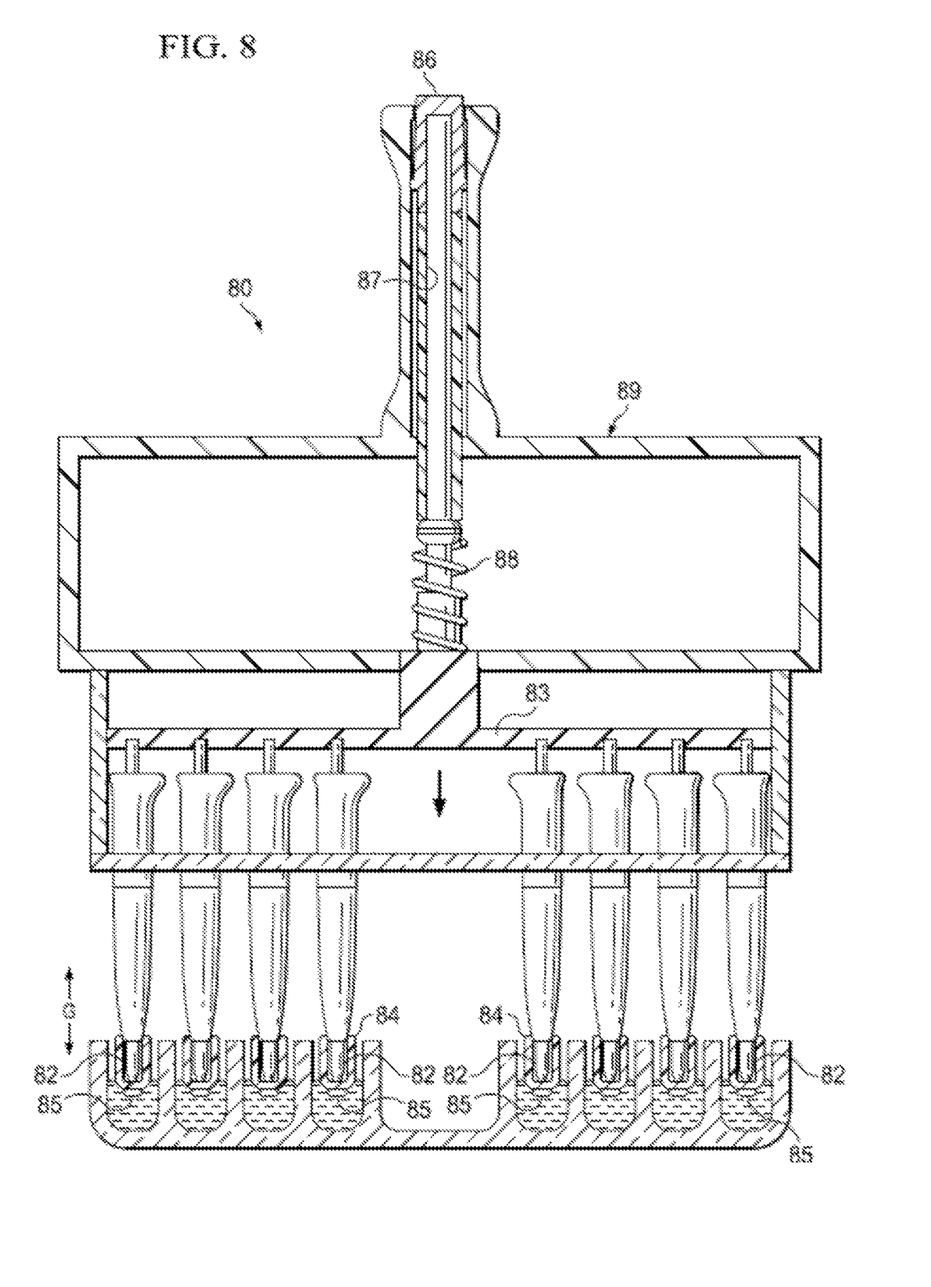
FIG. 8. Schematic of multi-magnetic cell pipettor, with or without springs.

FIG. 8 shows a variant embodiment of a multi-magnetic pipettor 80, which is actuated with a single button 86 which drives rod 87 and compresses spring 88 to actuate the second actuator 83, thus pushing 83 down (see arrow) and actuating a series of parallel pipettors each having magnet 82 shown depressed and inside cap 84, thus able to pick up cells 85. The entire device is contained in housing 89, which can be any suitable shape.

The magnetic pipettors can be coupled to robotic arms and used in high-throughput cell culturing, using standard or specially designed multiwell plates with 6, 12, 24, 48, 96, 384 and/or 1536, and the like.

Figures 9A, 9B:
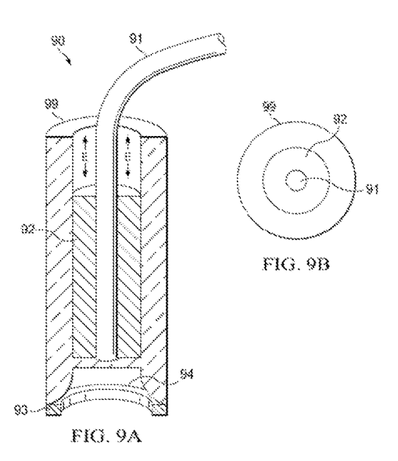

FIG. 9A shows a cross section of a fiber-optic coupled magnetic cell holder 90 wherein the actuators for moving the magnet is omitted for simplicity. It includes optical fiber 91, a non-adhering and non-magnetic cap 94 for use as a cell transfer surface. Magnet 92 can fit and slides in and out (-E-) of this cap 93, and is contained in housing 99. Optical fiber 91 fits in the center, through a ring magnet 92. An optical window 93 at the bottom of where cells will be magnetically held and light will be delivered and collected. This window could also comprise light filters for collecting a specific wavelength of light. FIG. 9B is a bottom view of fiber-optic coupled to magnetic cell holder.

In more detail, this fiber-optic coupled magnetic cell holder can be used to collect light resulting from fluorescence, chemi-luminescence, light scattering (elastic, Raman, surface enhanced Raman). The light signal can result from cells, nanoparticles, excreted proteins, and/or chemical substrates that are in the vicinity of the magnetized 3D cell cultures. This could be used to evaluate number of cells, cell viability, and cell proliferation and the like.

Figure 10:
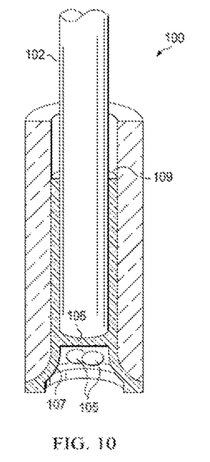
FIG. 10. Magnetic cell pipettor with more complex cap at the end for bringing multiple cultures into contact in a reproducible way, or guiding cells to center.

FIG. 10 shows a cross section of a magnetic cell holder 100 with more complex cap at the end for bringing multiple cultures into contact in a reproducible way, wherein the top of the holder is again omitted for simplicity. In FIG. 10, the magnet is 102, and the cap 107 has a flared end. The magnet slides up and down inside the cap or a guide portion of the cap 109, but is kept from touching the cells 105 by the cap base 106, which is the non-adhering surface that contacts and transfers cells.

The cap has a flared edge here, creating an enclosing shape, such as concave and cup-like (not limited to these), which assures cells and 3D cell cultures can be transferred inside the cup shape by surface tension, yet the space is sufficiently large so as to not disturb the structure of a nascent 3D cell culture, as would probably occur with the typical narrow tip pipette.

Figure 11:
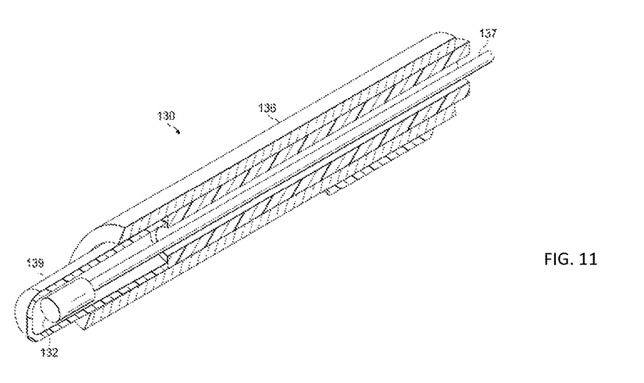
FIG. 11. Needle or catheter encased magnetic pipettor.

The components of FIG. 11 showing the schematic of a needle, hollow cylinder or catheter encased magnetic holder including a non-adhering and non-magnetic cap 139 for separating magnet 132 from cells. Magnet 132 can reversibly fit into this cap 139 and is found on the end of rod 137, which connects to an actuator (not shown) that raises and lowers the magnet 132 into the cap 139. Such means typically include buttons or levers, springs or other biasing force and detents or protrusions.

Fitting these components into a needle or catheter 136 allows the device to be used to puncture various materials, thus placing cells in very small places, such as for transfer of cells to an in vivo location (e.g., inside the cardiac muscles). The hollow cylinder or needle 136 also allows the device to be used to extract magnetized cells from 3D cultures, such as for extract of cells from different regions of a 3D culture, extract magnetized cell from an in vivo location carrying magnetized cells, and/or extract cells to generate an wound or hole on a 3D culture carrying magnetized cells.

Here we show the cap 139 fitting inside the needle 136, instead of over the outside edge as in a pipette tip, but either way is possible. However, fitting inside is preferred as this allows the cap 139 to slide up (refract) inside the needle 136 (retracted position not shown) during the puncture step. Means for retraction are not shown but are known in the art, in for example retractable pens and pipettes, and typically include a depressable button, spring or other biasing force, and detents or protrusions to hold the rod in the depressed position. The rod/magnet actuator and cap actuator means can also be combined (as in a dual color retractable pen), and dual detents, springs etc. and double buttons, and the like allow independent actuation of the two components.

These examples are illustrative only and not intended to unduly limit the invention as defined by the appended claims.

The invention claimed is:

1. A magnetic cell culture system, comprising
a cell culture vessel, and a cap shaped to fit over or under said cell culture vessel, said cap including a lip around an outer edge of said cap, wherein said lip fits over and surrounding an outer edge of said cell culture vessel, said cell culture vessel having one or more wells, and said cap having one or more depressions on said cap corresponding to a center of the one or more wells, wherein one or more magnets are affixed to said cap inside said one or more depressions such that said one or more magnets sit above or below said cell culture vessel and do not touch a media in said cell culture vessel,
wherein said cap comprises magnet position adjusters configured to adjust the position of said one or more magnets affixed into said one or more depressions in two or more of the three spatial directions, wherein the position of said one or more magnets can mechanically, electrically and/or magnetically be adjusted in said two or more of the three spatial directions, and wherein the cell culture vessel is a Petri dish, a cell culture flask, or a multiwell culturing plate.

2. The magnetic cell culture system of claim 1, wherein one of said magnet position adjusters of said cap is configured to adjust a height of said one or more magnets from said cell culture vessel.

3. The magnetic cell culture system of claim 1, wherein said cap is disc shaped, and wherein one of said magnet position adjusters of said cap includes a screwable collar that fits inside or outside said cap, so that unscrewing said collar functions to raise said cap from said cell culture vessel to a level and maintain said cap at the level while horizontally moving said one or more magnets by a second magnet position adjuster of said cap.

4. The magnetic cell culture system of claim 1, wherein said one or more magnets are reversibly fit into said one or more depressions.

5. The magnetic cell culture system of claim 1, wherein said cell culture vessel has multiple wells, and said one or more magnets are affixed to said cap at a center of each well of said multiple wells so that each well has a magnet.

6. The magnetic cell culture system of claim 1, wherein said one or more magnets are snap fit into said one or more depressions.

7. The magnetic cell culture system of claim 1, wherein said one or more magnets are adhered into said one or more depressions.

8. A magnetic cell culture vessel, comprising a vessel having a plurality of wells in an array, a cap covering said plurality of wells, said cap having a lip surrounding an outer edge of said vessel and a plurality of magnets in an array affixed to said cap, such that each well of said plurality of wells has a magnet of said plurality of magnets over or under said well at a center of said well and said magnet does not touch a media in said well when said cap sits in place over or under said vessel, wherein said cap comprises magnet position adjusters configured to adjust the position of said one or more magnets affixed into said one or more depressions in two or more of the three spatial directions, wherein the position of said one or more magnets can mechanically, electrically and/or magnetically be adjusted in the two or more of the three spatial directions, and wherein the vessel is a Petri dish, cell culture flask, or a multiwell culturing plate.

9. The magnetic cell culture vessel of claim 8, wherein said array of wells is an array of 6, 8, 12, 96, 384, or 1536 wells.

10. The magnetic cell culture vessel of claim 8, including a second cap that fits between said vessel and said cap.

11. A magnetic drive, comprising a cap sized to fit over or under an ANSI/SLAS microtiter plate having a plurality of wells, said cap having a lip around an outer edge thereof, said lip fitting around an outside edge of said ANSI/SLAS microtiter plate, said cap having a plurality of depressions having a plurality of magnets affixed thereinto, such that each well of said plurality of wells has a magnet of said plurality of magnets over or under said well at a center of said well when said magnetic drive is disposed over or under said ANSI/SLAS microtiter plate such that said magnet does not touch a media in said well, and wherein said cap comprises magnet position adjusters configured to adjust the position of said one or more magnets affixed into said one or more depressions in two or more of the three spatial directions, wherein the position of said one or more magnets can mechanically, electrically and/or magnetically be adjusted in said two or more of the three spatial directions.

12. The magnetic drive of claim 11, wherein each of said magnets having a Brmax of at least 12600 Gauss.

\* \* \* \* \*